(12) United States Patent
Ahmed et al.

(10) Patent No.: US 9,750,755 B2
(45) Date of Patent: *Sep. 5, 2017

(54) ANTIMICROBIAL COMPOSITIONS AND RELATED METHODS

(71) Applicant: DeLaval Holding AB, Tumba (SE)

(72) Inventors: Fahim U. Ahmed, Greensboro, NC (US); Alex Skender, Kansas City, MO (US); Chris Foret, Mission, KS (US); Thomas C. Hemling, Belton, MO (US); N. Camelia Traistaru, Kansas City, MO (US)

(73) Assignee: DeLaval Holding AB, Tumba (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/741,701

(22) Filed: Jun. 17, 2015

(65) Prior Publication Data

US 2015/0272969 A1    Oct. 1, 2015

Related U.S. Application Data

(63) Continuation of application No. 12/440,412, filed as application No. PCT/US2007/078054 on Sep. 10, 2007, now abandoned.

(60) Provisional application No. 60/888,243, filed on Feb. 5, 2007, provisional application No. 60/843,113, filed on Sep. 8, 2006.

(51) Int. Cl.

| | |
|---|---|
| *A61K 31/60* | (2006.01) |
| *A61K 31/192* | (2006.01) |
| *A61K 31/375* | (2006.01) |
| *A01N 37/02* | (2006.01) |
| *A61K 9/00* | (2006.01) |
| *A61K 9/12* | (2006.01) |
| *A61K 31/095* | (2006.01) |
| *A61K 31/19* | (2006.01) |
| *A61K 31/191* | (2006.01) |
| *A61K 31/194* | (2006.01) |
| *A61K 31/20* | (2006.01) |
| *A61K 31/201* | (2006.01) |
| *A61K 47/08* | (2006.01) |
| *A61K 47/10* | (2017.01) |
| *A61K 47/12* | (2006.01) |
| *A61K 47/20* | (2006.01) |

(52) U.S. Cl.
CPC ............ *A61K 31/60* (2013.01); *A01N 37/02* (2013.01); *A61K 9/0017* (2013.01); *A61K 9/12* (2013.01); *A61K 31/095* (2013.01); *A61K 31/19* (2013.01); *A61K 31/191* (2013.01); *A61K 31/192* (2013.01); *A61K 31/194* (2013.01); *A61K 31/20* (2013.01); *A61K 31/201* (2013.01); *A61K 31/375* (2013.01); *A61K 47/08* (2013.01); *A61K 47/10* (2013.01); *A61K 47/12* (2013.01); *A61K 47/20* (2013.01)

(58) Field of Classification Search
CPC ..................................................... A61K 31/192
USPC ......................................................... 514/159
See application file for complete search history.

(56) References Cited

U.S. PATENT DOCUMENTS

| | | | |
|---|---|---|---|
| 4,945,110 A | 7/1990 | Brokken et al. | |
| 4,975,217 A | 12/1990 | Brown-Skrobot et al. | |
| 6,262,038 B1 | 7/2001 | Pierce et al. | |
| 6,379,685 B1 | 4/2002 | Richter et al. | |
| 6,472,358 B1 | 10/2002 | Richter et al. | |
| 6,627,593 B2 * | 9/2003 | Hei ........................ | A01N 37/16 424/405 |
| 6,663,902 B1 | 12/2003 | Hei et al. | |
| 6,686,324 B2 | 2/2004 | Ramirez et al. | |
| 6,803,057 B2 | 10/2004 | Ramirez et al. | |
| 6,812,196 B2 | 11/2004 | Rees et al. | |
| 7,494,963 B2 | 2/2009 | Ahmed et al. | |
| 8,246,906 B2 | 8/2012 | Hei et al. | |
| 8,778,369 B2 | 7/2014 | Ahmed et al. | |
| 2002/0142051 A1 | 10/2002 | Rochon | |
| 2004/0157931 A1 | 8/2004 | Ra et al. | |
| 2004/0186037 A1 | 9/2004 | Cheung et al. | |
| 2007/0027119 A1 | 2/2007 | Ahmed et al. | |

FOREIGN PATENT DOCUMENTS

| | | |
|---|---|---|
| CA | 2361741 | 5/2003 |
| CA | 2454437 | 6/2005 |
| EP | 1027827 | 5/1998 |
| GB | 734624 | 8/1955 |

(Continued)

OTHER PUBLICATIONS

European Office Action dated Nov. 5, 2010 for EP Application No. 07 814 786.5; filed Sep. 10, 2007; Applicant: Delaval Holding AB et al. (5 pages).

(Continued)

*Primary Examiner* — Layla Soroush

(74) *Attorney, Agent, or Firm* — Hovey Williams LLP

(57) ABSTRACT

A liquid antimicrobial composition comprising an organic acid and one or more anionic surfactants is disclosed. In one embodiment, the organic acid is lactic acid and the anionic surfactant is sodium octane sulfonate. In a preferred embodiment, the antimicrobial solution is formulated as a teat dip for lactating animals, particularly cows. In other embodiments, the antimicrobial compositions may be used in personal care, hard surface care including hard surface disinfection in households, food processing, hospitals, restaurants, hotels, showers, or topically as hand soaps, surgical scrubs, and hoof disease mitigators.

6 Claims, No Drawings

(56) References Cited

FOREIGN PATENT DOCUMENTS

| WO | 92/09260 | 6/1992 |
|---|---|---|
| WO | 9209260 | 6/1992 |
| WO | 03/003832 | 1/2003 |
| WO | 03067989 | 8/2003 |

OTHER PUBLICATIONS

European Office Action dated Aug. 6, 2012 for EP Application No. 07 814 786.5; filed Sep. 10, 2007; Applicant: Delaval Holding AB et al. (3 pages).
Office Action dated Oct. 9, 2012 in U.S. Appl. No. 12/440,412, filed May 28, 2010.
European Office Action dated Mar. 5, 2012, for EP Application No. 07 814 786.5; filed Sep. 10, 2007; Applicant: Delaval Holding AB et al. (5 pages).
Office Action dated Jul. 12, 2013 in U.S. Appl. No. 12/440,412, filed May 28, 2010.
Dychdala, G.R. "Surface-Active Agents: Acid-Anionic Compounds," Disinfection, Sterilization and Preservation, fourth edition, S. S. Block ed. pp. 256-262, 1991.
Third Party Submission filed against EP 07814786.5 on Jan. 13, 2014.
Appendix B to the Third Party Submission: Material Safety Data Sheet for Bio-Terge Pass, Nov. 22, 2013; and Stepanol WA-EXTRA product bulletin dated Jul. 2012.
Office Action dated Dec. 17, 2014 in U.S. Appl. No. 12/440,412, filed May 28, 2010.

* cited by examiner

ANTIMICROBIAL COMPOSITIONS AND RELATED METHODS

RELATED APPLICATIONS

This application is a continuation of U.S. patent application Ser. No. 12/440,412, which is a National Stage Entry under 35 U.S.C. §371 of International Application No. PCT/US2007/078054, filed Sep. 10, 2007, which claims the benefit of priority to commonly-owned and U.S. Provisional Patent Application Nos. 60/843,113, filed 8 Sep. 2006, and 60/888,243, filed 5 Feb. 2007, each of which is incorporated herein by reference.

BACKGROUND

1. Field of the Invention

The present invention pertains to antimicrobial compositions of the type that may be used to control or destroy pathogenic microorganisms. More particularly, various antimicrobial agents are shown to work with cooperative effects against microorganisms in a wide variety of applications.

2. Description of the Related Art

Antimicrobial compositions are used to reduce the risk of infection. For example, antimicrobials are used to disinfect surfaces in hospitals, lavatories, food preparation facilities, and offices. Other uses include the control of pathogenic organisms on skin, where they may be used to reduce the transmission of disease or infection, e.g., as surgical scrub solutions or hand sanitizers. Antimicrobial compositions may also be used in veterinary applications for the control or prevention of hoof diseases, mastitis (in milk producing animals), or topical infections. Prevention of mastitis is a major goal of the dairy industry, where the disease may result from contact of the bovine or ovine mammary gland with pathogenic microorganisms, usually bacteria but occasionally yeast or fungi.

Mastitis is the single most costly disease affecting the dairy industry. Annual economic losses due to mastitis approximate $185 per dairy animal. This totals to approximately $1.7 billion annually for the entire United States market. Mastitis is always a potentially serious infection. Severe cases may cause death to the dairy animal. Milder cases are more common, but may have serious consequences, such as long term damage to the animal, loss of milk production for the dairy farmer and an unacceptable increase in veterinary costs.

To reduce mastitis, commercial teat dips have been developed which are usually administered to the teat by dipping, foaming, or spraying the teat prior to milking as well as after removal of the milking cup. Teat dips applied subsequent to milking may be in the form of lower viscosity dippable or sprayable compositions or in the form of a thick composition, film or barrier that remains on the teat until the next milking, which is generally 8 to 12 hours later.

Commercially available teat dips may be divided into two primary classifications, namely, non-barrier and barrier dips. The non-barrier teat dips are strictly antimicrobial and are applied to kill microorganisms that are already present in the teat canal or on the surface of the teat skin. By design, the microbiological effect is substantially immediate, targeting the contagious organisms that may be transferred between animals during the pre-milking, milking and post-milking process. The barrier dips may also be antimicrobial and are applied to form a prophylactic film or coating that may prevent microbes from contacting the teat. It is desirable to have an antimicrobial effect that remains active during the inter-milking period.

Teat dips have used a variety of antimicrobial agents. U.S. Pat. No. 2,739,922 issued to Shelanski describes the use of polymeric N-vinyl pyrrolidone in combination with iodophors. U.S. Pat. No. 3,993,777 issued to Caughman et al. describes the use of halogenated quaternary ammonium compounds. U.S. Pat. No. 4,199,602 issued to Lentsch describes the use of iodophors, chlorine releasing compounds (e.g. alkali hypochlorite), oxidizing compounds (e.g. hydrogen peroxide, peracids), protonated carboxylic acids (e.g. heptanoic, octanoic, nonanoic, decanoic, undecanoic acids), and nitroalkanols. U.S. Pat. No. 4,434,181 issued to Marks, Sr. et al. describes the use of acid anionics (e.g. alkylaryl sulfonic acids), chlorine dioxide (from alkali chlorite), and bisbiguanides such as chiorhexidine.

Some of the available teat dip agents suffer from serious drawbacks. For example, iodine, hypochlorite, chlorine dioxide, and hypochlorous acid are powerful disinfectants and strong oxidants, but they are also particularly noxious for both humans and animals. Chlorhexidine, for example, has become the focus of regulatory concern. Additionally, the use of overly powerful disinfectants may contribute to the mastitis problem by causing irritation of the teat skin, thus providing an opportunistic site which promotes infection. The Lentsch '602 patent recognizes that iodophors and such chlorine-based biocides as hypochlorite, chlorine dioxide, and hypochlorous acid have achieved the widest commercial acceptance; however, teat dips of the future may have to be iodine-free. Furthermore, the iodine-based and chlorine-based compositions may induce sensitized reactions in cow teats. This issue is of particular importance for barrier type products where the biocide may remain in contact with the skin during the 8-12 hour inter-milking period. On the other hand, less powerful teat dip agents, such as fatty acids and anionic surfactants, are often not broad enough in their antimicrobial spectrum to provide complete germicidal protection.

From a consumption point of view, it is known that relatively small quantities of iodine and chlorhexidine can result in taste changes of the milk as well as problems in the manufacture of dairy products. Furthermore, milk products must meet food and drug regulations which take into consideration ingestion of residual teat dip agents. There may be concern, for example, about increased iodine consumption because iodine is linked to thyroid function and it is recommended that some populations, such as pregnant women, limit their intake. Also, iodine associates with problems of staining, and some operators/users develop allergic symptoms such as skin irritation and sensitization from iodine-based product use.

There is a need for compositions that are effective broad spectrum antimicrobials that provide extended germicidal activity and are non-irritating to skin.

SUMMARY

In embodiments, the invention is an antimicrobial composition comprising an organic acid and an anionic surfactant. In one embodiment the composition is adapted for topical applications on an animal. In other embodiments, the invention is a method of using an antimicrobial composition comprising an organic acid and an anionic surfactant substantially reduces microbial concentrations, which may relate to the treatment or prevention of mastitis. Those skilled in the art will appreciate additional objects and advantages in the detailed description below. All references specifically disclosed in this specification are hereby incorporated by reference.

DETAILED DESCRIPTION

There will now be shown and described as a particular embodiment, an antimicrobial liquid composition that contains an organic acid mixed with an anionic surfactant. The organic acid, e.g., lactic acid, may be mixed with a carrier that is formulated according to the intended environment of use.

As used herein, the term "organic acid" means an organic compound that is an acid. The most common examples are the carboxylic acids having an acidity that derives from a carboxyl group —COOH. Other groups may also impart weak acidity, especially hydroxyl (—OH) groups, thiol (—SH) groups, enol groups (—C=C(OH)—), sulfate groups (—OSO$_3$H), sulfonate groups (—SO$_3$H) and phenols. Preferred organic acids have a carbon number less than twenty, and this number is even more preferably less than ten. The organic acids may be aliphatic, aryl, aromatic, unsubstituted or substituted with functional groups. The substituent(s) may be attached to any position of the carbon chain or carbon ring. The organic acid may, for example, include lactic acid, salicylic acid, tartaric acid, citric acid, glycolic acid, ascorbic acid, maleic acid, succinic acid, mandelic acid, dodecylbenzenesulfonic acid, propionic acid, gluconic acid, malic acid, benzoic acid, aspartic acid, acetic acid, oxalic acid, glutamic acid, adipic acid, hexanoic acid, octanoic acid, nonanoic acid, decanoic acid, undecanoic acid and combinations thereof. In another aspect, inorganic acids having pK$_a$ characteristics approximating those of organic acids may also be used. In one such example, sulfamic acid may be used. Lactic acid is particularly preferred as the organic acid for the disclosed compositions, as will be shown in detail later.

The compositions reported herein involve the discovery, hitherto unreported, that unexpectedly effective antimicrobial protection can be obtained when an organic acid, e.g., lactic acid, is combined with an anionic surfactant. Sodium Octane Sulfonate (SOS) and Sodium Lauryl Sulphate (SLS) are included in specific embodiments. The selection of these particular ingredients for testing should not, however, is considered a limiting factor because numerous other surfactants could be used which would still fall within the scope of the invention. For example, Sodium Lauryl Ether Sulfate (SLES) has been used in combinations with SOS and/or SLS with success. Further, other anionic surfactants could be used in other embodiments which would fall within the scope of the invention. Some examples of preferred anionic surfactants include but are not limited to alkyl sulfonates, secondary alkane sulfonates, alkyl sulfates, alkyl ether sulfates, aryl sulfonates, aryl sulfates, alkylaryl sulfonates, alkylaryl sulfates and alkyl ether sulfonates. Some examples of such anionic surfactants that are suitable are: alkali lauryl sulfates, alkali dodecylbenzenesulfonates, alkali octane sulfonates, alkali secondary alkane sulfonates, alkali lauryl ether sulfates and ammonium salts thereof.

Thus, the disclosures of specific embodiments herein should not be interpreted as requiring any particular anionic surfactant.

In one aspect, an antimicrobial composition contains an antimicrobial agent which is an organic acid, and a second agent which includes one or more anionic surfactants. In an embodiment, the agents are included in a pharmaceutically acceptable carrier, which may, for example, be water.

The carrier may include one or more additives selected from a buffering agent, an emollient, a humectant, a preservative, a barrier forming agent, a surfactant or wetting agent, a foaming agent, a viscosity control agent, a colorant, an opacifying agent, a skin conditioning agent and any combinations thereof.

The antimicrobial compositions provide a substantial reduction in Gram positive and Gram negative bacteria, as well other numerous classes of microbes. For particular embodiments, the reduction may be on the order of a three or four log reduction or a substantially complete kill that is greater than a five log (99.999%) reduction. In other embodiments, the kill counts could be higher or lower.

A broader object of the disclosed instrumentalities is to provide an antimicrobial composition that may be used, for example, according to any purpose for antimicrobial or bactericidal properties. In a particular embodiment, the composition is intended to be used as a teat dip. In other embodiments the composition is intended to be used as a hand sanitizer, a skin cleanser, a surgical scrub, a wound care agent, a disinfectant, a mouthwash, a bath/shower gel, a hard surface sanitizer and the like. Preferred compositions for skin applications have a pH of about 2.0 to about 8.0 and provide a substantial reduction, e.g., greater than a five log reduction (99.999%), in Gram positive and Gram negative bacterial populations. In even more preferred embodiments, the composition could have pH in the range of about 2.5 to 7.5. Further, different uses may prompt different pH targets. For example, compositions adapted for hard surfaces may be provided with lower pH values, such as 2.0 or 1.0.

Another object is to provide a composition which, when applied, results in a wound healing effect. The composition assists in a faster and qualitatively improved healing of wounds by decreasing the number of microorganisms in the vicinity of the wound. Further, the compositions are non-irritating.

Methods of preparing compositions may involve dissolving a desired concentration of antimicrobial agents and, optionally, any desired additives in a selected pharmaceutical carrier. The solution is then mixed, for example in a mixer, to form a final antimicrobial composition.

For some embodiments, the concentrations are those where the percentage of each functional ingredient or mixture of ingredients including antimicrobial agents by total weight of the composition is preferably from about 0.02 to 30% of each antimicrobial agent and 70 to 99.98% of a pharmaceutical carrier and other additives combined; more preferably from about 0.03 to 25% of each antimicrobial agent and from about 75 to 99.97% of a pharmaceutical carrier and other additives combined; and most preferably from about 0.04 to 20% of each antimicrobial agent and from about 80 to 99.96% of a pharmaceutical carrier and other additives combined, and still more preferably from about 0.05 to 15% of each antimicrobial agent and from about 85 to 99.95% of a pharmaceutical carrier and other additives combined.

As used herein, the term "subject" shall include humans and terrestrial animals. For example, the subject can be a domestic livestock species, a laboratory animal species, a zoo animal, a companion animal or a human. In a particular embodiment, "subject" refers more specifically to any lactating animal. In one embodiment, the subject is a cow.

The phrase "therapeutically effective amount" is intended to qualify the amount of the topical composition which will achieve the goal of decreased microbial concentration.

"Therapeutically effective" may also refer to improvement in disorder severity or the frequency of incidence over no treatment.

The term "topical" shall refer to any composition which may be applied to the epidermis or other animal portion on which compositions might be applied. Topical shall also refer to compositions used as mouthwashes.

The term "additive" shall mean any component that is not an antimicrobial agent or a pharmaceutical carrier. A pharmaceutical carrier is generally a bulk solvent used to dilute or solubilize the components of the composition, e.g., water.

The terms "teat dip" or "teat dipping" shall be interpreted broadly and in accordance with the terminology used in the art of dairy farming. Thus, the composition is not only intended for dipping of the teats but it can, of course, be applied in other ways, such as by spraying or foaming and still fall within the recognized terms teat dip or teat dipping composition or agent.

As used herein unless otherwise specified, the term "antimicrobial" describes a biocidal effect that may be, for example, an antibacterial, antifungal, antiviral, bacteriostatic, disinfecting, or sanitizing effect.

As shown in the examples below, combinations of the antimicrobial agents may include an organic acid (e.g., lactic acid) with an anionic surfactant or a mixture of anionic surfactants to make effective biocidal compositions. These antimicrobial ingredients may be formulated using additional antimicrobial agents, barrier-forming agents, foaming agents, viscosity control agents, pH adjusting agents, wetting agents, opacifying agents, skin conditioning agents and carriers to make a wide variety of products.

Additional Antimicrobial Agents

Traditional antimicrobial agents are the components of a composition that destroy microorganisms or prevent or inhibit their replication. In one aspect, the combined organic acid/anionic surfactant(s) antimicrobial embodiments discussed above may be used to replace or eliminate the need for traditional antimicrobial agents in a wide variety of applications. In another aspect, antimicrobial compositions according to the disclosed embodiments below may be used in combination with these traditional antimicrobial agents, for example, to achieve an effective kill at lower concentrations of traditional antimicrobial agents.

Traditional antimicrobial agents include iodophors, quaternary ammonium compounds, hypochlorite releasing compounds (e.g. alkali hypochlorite, hypochlorous acid), oxidizing compounds (e.g. peracids and hypochlorite), protonated carboxylic acids (e.g. heptanoic, octanoic, nonanoic, decanoic, undecanoic acids), acid anionics (e.g. alkylaryl sulfonic acids, aryl sulfonic acid, alkyl sulfonic acids, alkylaryl sulfuric acid, aryl sulfuric acid, alkyl sulfuric acid, alkylaryl sulfuric acid), chlorine dioxide from alkali chlorite by an acid activator, and bisbiguanides such as chlorhexidine. Phenolic antimicrobial agents may be chosen from 2,4,4"-trichloro-2'-hydroxydiphenylether, which is known commercially as triclosan and may be purchased from Ciba Specialty Chemicals as IRGASAN™ and IRGASAN DP 300™. Another such antimicrobial agent is 4-chloro-3,5-dimethyl phenol, which is also known as PCMX and is commercially available as NIPACIDE PX and NIPACIDE PX-P. Other traditional germicides include formaldehyde releasing compounds such as glutaraldehyde and 2-bromo-2-nitro-1,3-propanediol (Bronopol), polyhexamethyl biguanide (CAS 32289-58-0), guanidine salts such as polyhexamethylene guanidine hydrochloride (CAS 57028-96-3), polyhexamethylene guanidine hydrophosphate (89697-78-9), and poly[2-(2-ethoxy)-ethoxyethyl]-guanidinium chloride (CAS 374572-91-5) and mixtures thereof.

In one embodiment, the disclosed germicides may be used in combination with traditional germicides such as copper sulfate, zinc sulfate, sulfamethazine, quaternary ammonium compounds, hydrogen peroxide and/or peracetic acid, for example, to achieve an effective kill at lower concentrations of traditional germicides.

Barrier Forming Agents

Barrier and film forming agents are those components of a teat dipping composition that remain in contact with the teat between milking cycles. Barrier and film forming agents coat the teat skin and, optionally, the udder. Barrier agents may form a plug at the end of the open teat canal. Typical barrier and film forming agents include thick creams or emollients (made with viscosity control agents), films, polymers, latex and the like. Some nonionic surfactants may help further enhance the barrier properties of a composition, in addition to contributing to surface wetting. Examples of such surfactants may include, without limitation, polyoxyethylene-polyoxypropylene glycol (marketed as Pluronic F108). Another commonly used barrier agent is marketed as Pluronic P105. A latex material that provides an effective covering of the teat is described in U.S. Pat. No. 4,113,854. Suitable barrier forming agents include, for example, latex, arabinoxylanes, glucomannanes, guar gum, johannistree gums, cellulose, methyl cellulose, ethyl cellulose, hydroxyethyl cellulose, hydroxymethyl cellulose, carboxyethyl cellulose, carboxymethyl cellulose, starch, hydroxyethyl starch, gum arabic, curdlan, pullulan, dextran, polysulfonic acid, polyacryl amide, high molecular weight polyacrylate, high molecular weight cross-linked polyacrylate, carbomer, glycerol, sodium alginate, sodium alginate cross-linked with calcium salt, xanthan gum, poly(vinyl alcohol) (PVA) and poly(N-vinylpyrrolidone) (PVP). Preferred embodiments for barrier-forming agents include xanthan gum, carboxymethyl cellulose, sodium alginate, sodium alginate cross-linked with calcium salt, PVA, hydroxyethyl cellulose, PVP, and (2,5-dioxo-4-imidazolidinyl)-urea (Allantoin).

The compositions those are capable of forming a long-lasting persistent, continuous, uniform barrier film that is based upon modified polysaccharides when applied to the skin. The compositions have particular utility as barrier teat dips that are used prophylactically against mastitis. The barrier film-forming agent includes relatively low molecular weight polysaccharides, for example, as may be derived specifically from hydrolyzed starch.

The composition may be used for prophylactic treatment of a dairy animal's teats to provide a long lasting persistent protective germicidal barrier film that demonstrates persistence between milkings, and is controllably reproducible to yield a continuous, uniform persistent barrier. This treatment process entails milking the animal, coating the teats with the composition after milking, allowing the composition to dry and so also form a layer of persistent barrier film on the teats. The composition may be applied topically by painting, foaming, dipping or spraying. Furthermore, use of the composition is not limited to use against mastitis, and the composition may be used generally to treat or protect against any infectious skin condition.

A composition capable of forming a long-lasting, persistent, continuous, uniform barrier film may contain from about 0.1% to about 20% by weight of modified or hydrolyzed polysaccharide material for use as the barrier forming agent. The polysaccharide material has a majority polysaccharide component as starch, modified starch, hydrolyzed starch, a starch derivative, and combinations thereof. The majority polysaccharide components may have overall or average Dextrose Equivalence (DE) value ranging from 2 to 50, and this value more preferably ranges from 3 to 27. In this sense the term "majority polysaccharide component" is used to describe a majority weight percentage of all polysaccharides in the composition, i.e., more than 50% of all polysaccharides in the composition.

Foaming Agents

A foaming agent may be used in the disclosed antimicrobial compositions. A foaming agent aerates a liquid composition to produce a foam that may increase surface area of the composition and improve contact with the surface to be treated (e.g., an animal hoof). Typically, a foaming agent is in the form of a compressed gas, or a material that will decompose to release gas under certain conditions. Suitable gases include but are not limited to nitrogen, argon, air, carbon dioxide, helium and mixtures thereof. In addition, solid carbon dioxide (dry ice), liquid nitrogen, hydrogen peroxide and other substances that release gas via a change in state or through decomposition are contemplated for use with the present compositions. Typically, a high foaming surfactant such as sodium lauryl sulfate, dodecylbenzene sulfonic acid, sodium alkylaryl polyether sulfate, sodium lauryl ether sulfate, sodium decyl sulfate, cocamine oxide, $C_{12}$-$C_{14}$ whole coconut amido betaines can be used to generate a stable foam. The foam is produced when agitation in the form of a compressed gas is mixed with the solution either by bubbling the gas into the solution or spraying the solution or solution-gas mixture through spray equipment. Suitable gases include but are not limited to nitrogen, air, carbon dioxide and mixtures thereof. Foam can also be generated by the mechanical action of animals walking through the composition, or by other mechanical means that mix atmospheric air with the composition. The composition can be applied by having animals walk through an area containing the foam or by having the animal walk through a footbath solution that has foam floating on top of the solution.

Surfactants are well known for foaming and are widely used as foaming agents in hand soap and manual/hand dishwashing detergents and such surfactants can be used as foaming agents in applications where foaming can boosts the performance and increase contact time of the composition to particular substrates. Examples of such. Suitable anionic surfactants can be chosen from a linear alkyl benzene sulfonic acid, a linear alkyl benzene sulfonate, an alkyl α-sulfomethyl ester, an α-olefin sulfonate, an alcohol ether sulfate, an alkyl sulfate, an alkylsulfo succinate, a dialkylsulfo succinate, and alkali metal, alkaline earth metal, amine and ammonium salts thereof. Specific examples are linear $C_{10}$-$C_{16}$ alkyl benzene sulfonic acid, linear $C_{10}$-$C_{16}$ alkyl benzene sulfonate or alkali metal, alkaline earth metal, amine and ammonium salt thereof e.g. sodium dodecylbenzene sulfonate, sodium $C_{14}$-$C_{16}$ α-olefin sulfonate, sodium methyl α-sulfomethyl ester and disodium methyl α-sulfo fatty acid salt. Suitable nonionic surfactants can be chosen from an alkyl polyglucoside, an alkyl ethoxylated alcohol, an alkyl propoxylated alcohol, an ethoxylatedpropoxylated alcohol, sorbitan, sorbitan ester, an alkanol amide. Specific examples include $C_8$-$C_{16}$ alkyl polyglucoside with a degree of polymerization ranging from 1 to 3 e.g., $C_8$-$C_{10}$ alkyl polyglucoside with a degree of polymerization of 1.5 (Glucopon® 200), $C_8$-$C_{16}$ alkyl polyglucoside with a degree of polymerization of 1.45 (Glucopon® 425), $C_{12}$-$C_{16}$ alkyl polyglucoside with a degree of polymerization of 1.6 (Glucopon® 625). Amphoteric surfactants can be chosen from alkyl betaines and alkyl amphoacetates. Suitable betaines include cocoamidopropyl betaine, and suitable amphoacetates include sodium cocoamphoacetate, sodium lauroamphoacetate and sodium cocoamphodiacetate. Alkyl amine oxides based on C12-C14 alkyl chain length feedstock such as those derived from coconut oil, palm kernel oil is also suitable foaming agents.

Viscosity Control Agents

Viscosity control agents may be added to formulate the antimicrobial compositions according to an intended environment of use. In one example, it is advantageous for some compositions to have an optimized solution viscosity to impart vertical clinging of the product onto a teat. This type of viscous product, especially one having a suitable thixotropic, pseudoplastic or viscoelastic gel strength, minimizes dripping of the product to avoid wastage and is particularly advantageous in teat dip compositions. Teat dip compositions may benefit from a preferred dynamic viscosity ranging from 1 cPs to 3000 cPs. Other applications including hard surface disinfectants have a preferred dynamic viscosity ranging from about 1 cPs to 300 cPs. In another example, the amount of viscosity control agents may be substantially reduced or even eliminated in other compositions, such as surface or floor disinfectants where easy cleanup is desired. An intermediate or medium viscosity composition may be useful in a hand cleaner or personal care product. It is seen from these examples that the antimicrobial compositions may be formulated for a wide variety of applications by altering the amount of viscosity control agents. The viscosity referred to throughout this application is Brookfield viscosity measured in cPs by a Brookfield LV viscometer at ambient temperature (25° C.) with a spindle #2 @ 3 to 30 rpm. In various embodiments, a thickener may be added to achieve a viscosity range of from 50 cPs to 10000 cPs, or from 100 cPs to 4000 cPs.

Suitable viscosity control agents include hemicellulose, for example arabinoxylanes and glucomannanes; plant gum materials, for example guar gum and johannistree gums; cellulose and derivatives thereof, for example methyl cellulose, ethyl cellulose, hydroxypropyl cellulose, hydroxyethyl cellulose or carboxymethyl cellulose; starch and starch derivatives, for example hydroxyethyl starch or cross linked starch; microbial polysaccharides, for example xanthan gum, sea weed polysaccharides, for example sodium alginate, carrageenan, curdlan, pullulan or dextran, dextran sulfate, whey, gelatin, chitosan, chitosan derivatives, polysulfonic acids and their salts, polyacrylamide, and glycerol. Preferred viscosity controlling agents are, different types of cellulose and derivatives thereof, particularly hydroxyalkyl cellulose, methyl cellulose, and glycerol. High molecular weight (MW>1,000,000) cross-linked polyacrylic acid type thickening agents are the products sold by B.F. Goodrich (now Lubrizol) under their Carbopol® trademark, especially Carbopol® 941, which is the most ion-insensitive of this class of polymers, and Carbopol® 940 and Carbopol®934. The Carbopol® resins, also known as "Carbomer", are reported in U.S. Pat. No. 5,225,096, and are hydrophilic high molecular weight, cross-linked acrylic acid polymers. Carbopol® 941 has a molecular weight of about 1,250,000, Carbopol® 940 has a molecular weight of approximately 4,000,000, and Carbopol 934 has a molecular weight of approximately 3,000,000. The Carbopol® resins are cross-linked with polyalkenyl polyether, e.g. about 1% of a polyallyl ether of sucrose having an average of about 5.8 allyl groups for each molecule of sucrose. Further detailed information on the Carbopol® resins is available from B.F. Goodrich (Lubrizol), see for example, the B. F. Goodrich catalog GC-67, Carbopol® Water Soluble Resins. Clays and modified clays such as bentonite or laponite can also be used as thickeners. Co-thickeners are often added to improve the stability of the gel matrix, for example, colloidal alumina or silica, fatty acids or their salts may improve gel stability. Typical viscosity control ingredients include xanthan gum, carboxymethyl cellulose, sodium alginate, sodium alginate cross-linked with calcium salt, polysulfonic acids and their salts, polyacrylamide, polyvinyl alcohol (PVA), hydroxyethyl cellulose and polyN-vinylpyrrolidone) (PVP).

Buffering and pH Adjusting Agents

A composition pH value may be selectively adjusted by the addition of acidic or basic ingredients. Generally, an acidic pH is preferred. Suitable acids for use as pH adjusting agents may include, for example, citric acid, acetic acid, lactic acid, phosphoric acid, phosphorous acid, sulfamic acid, nitric acid, nitrous acid and hydrochloric acid. It will be recognized by those skilled in the art that the organic acid, e.g., lactic acid, selected as the antimicrobial organic acid will also influence pH, and thus, have an adjusting effect as discussed in this paragraph. Mineral acids may be used to drastically lower the pH. The pH may be raised or made more alkaline by addition of an alkaline agent such as sodium hydroxide, potassium hydroxide, sodium carbonate, sodium bicarbonate, monosodium acid diphosphonate or combinations thereof. Traditional acid buffering agents such as citric acid, lactic acid, phosphoric acid may also be used to maintain a desired pH. The pH value of the composition may be adjusted by the addition of acidic or basic or buffering materials.

The physical property of pH may be adjusted by acid or base addition, and is broadly preferred in the range of from 2.0 to 8.0 for use in teat dip compositions and other compositions that are intended to contact the skin. In a more preferred sense this range is from 2.0 to 5.0, and a still more preferred range is from 2.5 to 4.5. Hard surface and commercial disinfectants may be provided with lower pH values, such as 2.0 or 1.0.

Wetting Agents

Wetting agent(s) or surface active agent(s) are also known as surfactants. Typical wetting agents are used to wet the surface of application, reduce surface tension of the surface of application so that the product can penetrate easily on the surface and remove unwanted soil. The wetting agents or surfactants of the composition increase overall detergency of the formula, solubilize or emulsify some of the organic ingredients that otherwise would not dissolve or emulsify, and facilitate penetration of active ingredients deep onto the surface of the intended application surfaces, such as teat skin.

Suitably effective surfactants used for wetting may include anionic, cationic, nonionic, zwitterionic and amphoteric surfactants. Wetting agents and surfactants used in the inventive applications can be high foaming, low foaming and non foaming type. Suitable anionic surfactants can be chosen from a linear alkyl benzene sulfonic acid, a linear alkyl benzene sulfonate, an alkyl α-sulfomethyl ester, an α-olefin sulfonate, an alcohol ether sulfate, an alkyl sulfate, an alkylsulfo succinate, a dialkylsulfo succinate, and alkali metal, alkaline earth metal, amine and ammonium salts thereof. Specific examples are linear $C_{10}$-$C_{16}$ alkyl benzene sulfonic acid, linear $C_{10}$-$C_{16}$ alkyl benzene sulfonate or alkali metal, alkaline earth metal, amine and ammonium salt thereof e.g. sodium dodecylbenzene sulfonate, sodium $C_{14}$-$C_{16}$ α-olefin sulfonate, sodium methyl α-sulfomethyl ester and disodium methyl α-sulfo fatty acid salt. Suitable nonionic surfactants can be chosen from an alkyl polyglucoside, an alkyl ethoxylated alcohol, an alkyl propoxylated alcohol, an ethoxylatedpropoxylated alcohol, sorbitan, sorbitan ester, an alkanol amide. Specific examples include $C_8$-$C_{16}$ alkyl polyglucoside with a degree of polymerization ranging from 1 to 3 e.g., $C_8$-$C_{10}$ alkyl polyglucoside with a degree of polymerization of 1.5 (Glucopon® 200), $C_8$-$C_{16}$ alkyl polyglucoside with a degree of polymerization of 1.45 (Glucopon® 425), $C_{12}$-$C_{15}$ alkyl polyglucoside with a degree of polymerization of 1.6 (Glucopon® 625), and polyethoxylated polyoxypropylene block copolymers (poloxamers) including by way of example the Pluronic® poloxamers commercialized by BASF Chemical Co. Amphoteric surfactants can be chosen from alkyl betaines and alkyl amphoacetates. Suitable betaines include cocoamidopropyl betaine, and suitable amphoacetates include sodium cocoamphoacetate, sodium lauroamphoacetate and sodium cocoamphodiacetate.

It will be recognizable to those skilled in the art that because at least one surfactant (e.g., an anionic surfactant) is included as a synergistic antimicrobial agent in this composition, that these surfactants would also have an influence on the wetting properties of the mixture.

Opacifying Agents and Dyes

An opacifying agent or dye is optionally included in the present compositions. For example, color on a teat tells a farmer that a particular cow has been treated. To preclude any problems with possible contamination of milk, it is preferred that only FD&C Certified (food grade) dyes be used. There are many FD&C dyes available which are FD&C Red #40, FD&C Yellow #6, FD&C Yellow #5, FD&C Green #3 and FD&C Blue #1. Dyes used either alone or in combination are preferred. D&C Orange #4 can also be used. Titanium dioxide ($TiO_2$) is widely used as an opacifier and can also be used in combination with various colorants.

Preservatives

Some known teat dips and hand sanitizers include ethylenediaminetetraacetic acid (EDTA) and/or its alkali salts which can act as a chelating agent to remove metal ions from hard water. The metal ions, if not removed from the composition, serve as reaction sites for enzymes within the bacteria; the metalloenzyme reactions produce energy for bacterial cell replication. Other traditional preservatives are widely used, for example, paraban, methyl paraban, ethyl paraban, glutaraldehyde, etc. Preservatives such as an alcohol can also be added. The alcohol, in embodiments, may be benzyl alcohol, a low molecular weight alcohol having a carbon number less than five, and combinations thereof.

Skin Conditioning Agents

Skin conditioning agents may also be optionally used in the disclosed compositions. Skin conditioning agents may provide extra protection for human or animal skin prior to or subsequent to being exposed to adverse conditions. For example, skin conditioning agents may include moisturizers, such as glycerin, sorbitol, propylene glycol, D-Panthenol, Poly Ethylene Glycol (PEG) 200-10,000, Poly Ethylene Glycol Esters, Acyl Lactylates, Polyquaternium-7, Glycerol Cocoate/Laurate, PEG-7 Glycerol Cocoate, Stearic Acid, Hydrolyzed Silk Peptide, Silk Protein, Aloe Vera Gel, Guar Hydroxypropyltrimonium Chloride, Alkyl Poly Glucoside/Glyceryl Luarate, shea butter and coco butter; sunscreen agents, such as titanium dioxide, zinc oxide, octyl methoxycinnamate (OMC), 4-methylbenzylidene camphor (4-MBC), oxybenzone and homosalate; and itch-relief or numbing agents, such as aloe vera, calamine, mint, menthol, camphor, antihistamines, corticosteroids, benzocaine and paroxamine HCl.

Pharmaceutical Carriers

A typical carrier or matrix for an antimicrobial composition is deionized water, although one skilled in the art will readily understand that other solvents or compatible materials other than water may be used to achieve the effective concentrations of germicidal agents. In some embodiments, a composition may contain at least about 60% water and preferably at least about 70% water by weight based on the total weight of the composition. Propylene glycol, glycol ethers and/or alcohols can also be used as a carrier either alone or in combination with water.

Materials and Reagents

The test bacteria were *Eschericia coli* (ATCC 11229), which were originally isolated from mastitis infection and obtained on commercial order from Mastitlaboratoriet, SVA, and *Staphococcus aureus* (ATCC6538 from Microbiologics, St. Cloud, Minn.), which was also isolated from mastitis infection.

Testing of Antimicrobial Activity

Various standardized test methods are in place for comparatively testing the efficacy of antimicrobial agents. The preferred standard is defined as AOAC Official Method 960.09, as published by the Association of Analytical Chemists (AOAC International) in 2000 (Association of Official Analytical Chemists. 1990 (Official Methods of Analysis, Pages 138-140 in Germicidal and Detergent Sanitizing Action of Disinfectants 960.09, Vol. I. 15$^{th}$ ed. AOAC, Arlington, Va.). Europeans tend to use other standards for this same purpose, such as the EN1040, EN1656 and EN 14885 test methods. All of these standards are incorporated by reference to the same extent as though fully disclosed herein.

According to a modified EN1656 dilution neutralization method, freeze dried *E. coli* (ATCC 11229) and *S. aureus* (ATCC 6538) were hydrated, grown for four days and transferred. Then bacteria were diluted to form a suspension to have an initial concentration of about $10^8$ cfu/mL.

Freeze-dried pellets of *E. coli* (ATCC 11229) and *S. aureus* (ATCC 6538) were hydrated, placed in test tubes containing nutrient agar and incubated at 37° C. for 24 hours. Sterile buffer (0.25 M phosphate adjusted to pH 7.2) was used to dilute and transfer the bacteria to additional nutrient agar tubes, which were incubated for another 24 hours. *S. aureus* was then diluted with buffer and transferred to nutrient agar in French bottles, and *E. coli* was diluted and transferred to fresh nutrient agar tubes. Both types of bacteria were incubated at 37° C. for 72 hours. *E. coli* was then diluted and transferred to nutrient agar in French bottles. Sterile buffer and glass beads were added to the *S. aureus* French bottles and the solution was vacuum filtered through a #2 filter. The resulting bacterial suspension had a concentration of approximately $10^8$ cfu/mL. After 24 hours, the *E. coli* suspension was collected in the same manner. Sterilized skimmed milk was used as an interfering substance in all testing instead of bovine albumin as in EN 1656 protocol. One mL of milk and 1 mL of bacterial suspension were mixed and left in contact for 2 minutes at 25° C. Eight mL of the solutions described below in Tables 1 and 2 were then added to the mixture and left in contact for 30 seconds at 25° C. One milliliter of the resulting solution was removed and diluted with 9 mL of phosphate buffer at pH 7.2, and then four successive dilutions were made. Samples from each dilution were plated in duplicate and agar was added. One mL of the previous mixture was added to 9 mL of neutralizing solution and then mixed. Three serial dilutions were made of this solution and 1 mL of each solution was dispensed into a Petri dish in duplicate. Also, 0.1 mL of the most dilute solution was dispensed in duplicate. Approximately 15 mL of sterile tryptone glucose extract agar was added to each Petri dish and when solidified, each plate was incubated at 37° C. for 48 hours. This procedure was repeated for all samples to be tested.

For controls, the $10^8$ cfu/mL bacteria suspensions were diluted to concentrations of $10^4$ and $10^3$ cfu/mL. One milliliter of the $10^4$ cfu/mL dilutions and 0.1 mL of the $10^3$ cfu/mL dilutions (done in triplicate) were dispensed onto Petri dishes and approximately 15 mL of tryptone glucose extract agar was added. When solidified, the plates were incubated at 37° C. for 48 hours. An average of the plate counts for the triplicate platings of the $10^3$ cfu/mL dilution was considered the initial numbers control count.

The plates with bacterial populations between 25 and 250 were counted and results were expressed as logarithmic reductions according to EN 1656 test method.

Irritation Testing

As will be seen below, Blood Cell Irritation tests were performed to determine if some particular representative compositions would be mild enough for topical applications. These tests involved separating red blood cells and then exposing them to the compositions. The tests used for the compositions addressed in Tables 1-2 included two measurements made on cow's blood. In the tests, fresh calf blood samples were obtained; 50 mL of sodium citrate buffer (17.03 g trisodium citrate+8.45 g citric acid diluted to 1 L with bacteria-free DI water) was added to every 450 mL of blood and mixed. The blood was then centrifuged to isolate red blood cells (RBC), which were then washed with sodium citrate buffer, and centrifuged several times to remove white cells and plasma, according to a known method. The red blood cells were placed into containers for use in testing the disclosed antimicrobial compositions.

Red blood cells were treated with water, centrifuged and then, using a UV spectrophotometer, the absorption at 560 nm was measured in order to determine complete cell denaturation (H100). The product to be tested was then diluted in the range of 5000 ppm to 60000 ppm, blood cells were added to these dilutions, centrifuged and the absorption at 560 nm was measured by UV spectrometry. Haemolysis Values (H50) were determined by plotting absorption versus concentration. The H50 value represents the product concentration (expressed in ppm) at which half of the blood cells are denatured.

Product Haemolysis Values (H50); Product Denaturation Index Values (DI); and Lysis/Denaturation Ratios (LID) were determined for the compositions using known methods. Descriptions of these methods were disclosed by Wolfgang J. W. Pape, Udo Hoppe: In vitro Methods for the Assessment of Primary Local Effects of Topically Applied Preparations, *Skin Pharmacol.* (1991), 4, 205-212, which is incorporated herein by reference. The haemolysis—or tendency of the red blood cells to rupture when in contact with the test product—was measured by the half-haemolysis value H50. The denaturation of protein caused by the test product was measured by the denaturation index (DI). For DI measurements, a 1000 ppm solution of sodium lauryl sulfate solution was used as a reference. The overall irritation value for a product was determined by the ratio of the H50/DI which is referred to as the lysis/denaturation quotient. The overall irritation score is given by the lysis/denaturation value which is calculated by the equation: L/D=H50 (measured in ppm)/DI (measured in %).

The H50 score which measures haemolysis alone usually shows a similar irritation correlation to the L/D ratio. The higher the ppm value for H50 the less irritating the product.

A crude scale is H50>500 ppm (non-irritant); 120-500 (slight irritant), 30-120 (moderate irritant), 10-30 (irritant), 0-10 (strong irritant).

The DI score which measures denaturation of protein also shows a correlation to the L/D ratio. A crude scale is DI 0-5% (non-irritant); 5-10% (slight irritant), 10-75% (moderate irritant), 75-100% (irritant), and >100% (strong irritant).

Although the H50 and DI values may be of use in the interpretation of the results, the LID ratio is the primary value used to determine irritation. This method is best suited to comparing two or more products and determining which product is likely to cause the least irritation to skin and eyes. In terms of indication, an L/D value greater than 100 is an indication that the composition is a non-irritant; levels between 10 and 100 are considered slight irritants; levels between 1 and 10 are considered moderate irritants; levels between 0.1 to 1 are considered irritants; and levels lower than 0.1 are considered strong irritants.

Results

Historically, combinations of organic acids and surfactants in topical solutions evidenced little antimicrobial efficacy. In some of these instances, the additives interfered with the efficacy. Thus, even when successful kills might be obtained using lactic acid along with a surfactant in an aqueous solution, that effectiveness would diminish when the application required additives (e.g., viscosity control and opacifying agents, barrier forming agents, etc.). This interference made these combinations unsuitable for real-world applications. Especially ones in which some contact with animal skin is intended (e.g., teat-dip topical germicides).

Through experimentation, it has been discovered that anionic surfactants, and more specifically, certain anionic surfactants, when combined with lactic acid in a particular teat dip composition, provide a synergistic result enabling greater than five-log reductions (99.999%), while still avoiding conventional oxidizers which are more harmful to the animals' skin.

Shown below are the results of experiments carried out to determine the efficacy of various antimicrobial compositions against *E. coli* and *S. aureus*. The antimicrobial agents in the compositions disclosed below in Table 1 are comprised of lactic acid in combination with Sodium Octane Sulfonate (SOS) along with numerous additives which may be included in a product for topical use. One advantage attributable to SOS which is unrelated to efficacy is that it is entirely biodegradable and thus environmentally friendly. So much so, that SOS meets the European Surfactant Detergent Regulation requirements. This makes its inclusion in antimicrobial compositions more readily acceptable than other potential ingredients. Table 1 below shows the use of SOS with lactic acid. Each of the values in the Table is displayed as weight percentages (% w/w).

TABLE I

BARRIER TEAT DIP FORMULATIONS WITH LACTIC ACID AND SODIUM OCTANE SULFONATE

| Ingredients and Concentration (% w/w): Formulations Sequence | A | B | C | D | E |
|---|---|---|---|---|---|
| Water | 70.66 | 71.15 | 73.65 | 66.69 | 70.75 |
| Keltrol RD (Xantan Gum) | 0.40 | 0.40 | 0.40 | 0.40 | 0.40 |
| Maltodextrin (Maltrin M040) | 5.00 | 5.00 | 5.00 | 5.00 | 5.00 |
| Sorbitol 70% (Hexane-1,2,3,4,5,6-Hexaol) | 14.29 | | | 14.29 | |
| Glycerin | | 10.00 | 10.00 | | 10.00 |
| Allantoin (2,5-Dioxo-4-Imidazolidinyl) Urea | 0.10 | 0.10 | 0.10 | 0.10 | 0.10 |
| Polyoxyethylene-polyoxypropylene Glycol | 0.20 | 0.20 | 0.20 | 0.20 | 0.20 |
| Lactic Acid 88% USP (L(+)-2-Hydroxypropanoic acid) | 4.00 | 4.00 | 4.00 | 4.00 | 4.00 |
| Bioterge PAS-8S 38% (Sodium Octane Sulfonate | 5.30 | 7.90 | 5.30 | 7.90 | 7.90 |
| Sodium Hydroxide (50%) | 0.00 | 1.20 | 1.30 | 1.37 | 1.60 |
| FD&C Yellow # 5 | 0.03 | 0.03 | 0.03 | 0.03 | 0.03 |
| FD&C Blue # 1 | 0.02 | 0.02 | 0.02 | 0.02 | 0.02 |
| pH | 2.15 | 3.02 | 3.53 | 3.48 | 3.52 |
| Micro Test: EN 1 656, 30 Seconds contact.@25° C.: Results are in Log Reduction from Initial Bacteria Count $10^8$ cfu/mL | | | | | |
| *Staphyloccocus aureus* | 7.0 | 6.9 | 5.1 | 5.9 | 5.5 |
| *Echerichia coli* | 7.0 | 7.0 | 7.0 | 7.0 | 7.0 |
| Blood Cell Skin Irritation Test Results: | | | | | |
| Product Haemolysis Value (H50) (ppm) | 53,000 | 23400 | 46000 | 22,500 | 22,500 |
| Product Denaturation Index Value (DI) (%) | 19.3 | 9.1 | 11.2 | 7.7 | 11 |
| Lysis/Denaturation Ratio (L/D) (higher better) | 2,740.8 | 2585 | 4095.1 | 2,930 | 2,043 |
| Barrier/Film Quality: | Good | Wet | NA | Good | Good |

It should be recognized that each ingredient's concentration is 100% active unless that ingredient is expressly identified as having a certain percentage of active versus inert ingredients. For example, for the solutions used in Experiments A and D, the emollient sorbitol is disclosed to have a weight percentage of 14.29%. In terms of the active ingredient hexane-1,2,3,4,5,6-hexaol, however, the concentration is shown to be 70%. (See the description in the left margin of Table I). This means that the total hexane-1,2,3, 4,5,6-hexaol included in the compositions for experiments A and D is (0.7) times 14.29, or 10.00% in each of compositions A and D. In trials B, C and E, 10.0% glycerin was used instead of sorbitol. Since no concentration percentage is listed in the left-hand margin description for this ingredient, the concentration would be 100%, or 10.0% of the full solution. Similarly, the sodium hydroxide included in trials B-E would only be 50% as shown.

Partial concentrations of active ingredients are also revealed with respect to the antimicrobial components, lactic acid and anionic surfactant. As can be seen in the chart, the lactic acid ingredient used contains only 88% L (+)-2-hydroxypropanoic acid (the active portion). Thus, although each of trials A-G shows a 4.0% w/w concentration for lactic acid, only (0.88) times 4.0, or 3.52% of L(+)-2-hydroxypropanoic acid is included. With respect to SOS, the only anionic surfactant used in each of experiments A-E, the concentration of actual SOS in the Bioterge PAS-8S product used is 38%. Thus, for the trials which show a weight percentage of 5.3%, the percentage of actual SOS is only 2.0%, and for the rest of the experiments where the percentage is shown as 7.9%, the actual SOS included would be only 3.0%.

The relatively low percentages of SOS used in experiments A-E have been found to be surprisingly effective from a germicidal standpoint. As can be seen from Table I, the kill numbers for each of the compositions A-E were in excess of five log reductions for both *Staphyloccocus aureus* as well as *Echericia coli*. It can also be seen that the SOS and lactic acid are compatible with the additive package, and that neither the glycerin nor sorbitol, nor the thickening agent nor film forming agent, alternatives interfered with efficacy.

The results shown in Table I show superior kill results. The log reductions for *E. coli* were a seven log reduction in each instance. For *S. aureus*, at least five log reductions resulted, which are above industry standards, and in some cases the reductions were as high as seven log (total kill).

Lactic acid has poor, or marginally effective, germicidal properties against Gram positive and Gram negative bacteria when used as a sole antimicrobial agent. Only a moderate germicidal efficacy of lactic acid has been found, and only at very high concentrations. Typically, less than a three log reduction in *S. aureus* concentration and a five log reduction in *E. coli* concentration are attained after 30 seconds contact when 10% lactic acid is used alone. However, some non-ionic surfactants in combination with lactic acid have moderate to good germicidal efficacy, but most are skin irritants and are not suitable for topical skin care products. It has now been discovered that an organic acid (e.g., lactic acid) when combined with certain anionic surfactants can provide synergistic kill results—even when included with necessary additives which adapt it for use with topical applications.

The mildness to the animal's skin is of tremendous benefit when coupled with the outstanding germicidal effectiveness of the lactic acid/anionic surfactant combinations. As already discussed briefly above, traditional germicides that are presently used in skin care products, e.g., topical teat dip applications, are often based on iodine, iodophor, chlorine dioxide, or hypochlorite, which are all skin irritants. For this reason, conventional antimicrobials adapted for use on the skin include expensive and formulaically burdensome conditioning agents which are needed in the product to mask the skin irritation. Because the anionic surfactant and lactic acid combination used here is not a skin irritant, skin conditioning and moisturizing agents are at best unnecessary, and at least may be minimized in the product.

Tests also show that a reasonably high pH value (e.g., 3.0 or above) can be attained without negating the kill properties of the antimicrobial agents. This can be seen in particular with respect to compositions B-E. By maintaining a high pH value, the product is less offensive to the animal's skin.

The mildness of the product is quantified by the irritation results obtained. Of the compositions listed, only A, B, C, D and E were tested for irritation potential. As can be seen, the values measured for each of Product Haemolysis Value (1-150); Product Denaturation Index Value (DI); and Lysis/Denaturation Ratio (L/D) are within non-irritating ranges. For example, the H50 results for compositions A, B, C, D and E were 22,500 ppm or higher—well above the 500 ppm minimum for classification as a "non-irritant." Similarly, the DI value for sample A was 19.3 placing it as a moderate irritant may be due to its lower pH of 2.15, 9.1 for B and 7.7 for D placing both in the "slight irritant" category, whereas the DI value for sample C and E was 11.2 and 11, respectively, placing it near the lower range of the "moderate irritant" classification. With respect to L/D ratios, which are the primary value relied on to determine irritability, composition A, produced L/D ratio of 2741, composition B produced 2585, composition C produced 4095 whereas D and E produced ratios of 2930 and 2043, respectively—each over twenty times greater than the minimum threshold of 100 for being classified as a non-irritant. Thus, all of the parameters indicate that the lactic acid/SOS combination is an extremely effective antimicrobial, while being surprisingly mild to the skin.

The Table I results also reveal that most of the compositions scored well when rated for Barrier/Film Quality. Only compositions A, B, D, and E were evaluated using the testing methods discussed above. Of these, only sample B reflected a "wet" rating, whereas compositions A, D and E all resulted in "good" ratings, meaning that these compositions would perform well in teat dipping and other like topical applications because the composition will form a continuous coating that will remain in contact with the skin.

TABLE II

BARRIER TEAT DIP FORMULATIONS WITH LACTIC ACID, SODIUM LAURYL SULFATE AND SODIUM OCTANE SULFONATE

| Ingredients and Concentration (% w/w): Formulations Sequence | F | G | H | I | J | K | L | O | P |
|---|---|---|---|---|---|---|---|---|---|
| Water | 65.73 | 67.06 | 67.73 | 68.39 | 66.40 | 67.39 | 67.16 | 68.41 | 66.51 |
| Keltrol RD (Xantan Gum) | 0.40 | 0.40 | 0.40 | 0.40 | 0.40 | 0.40 | 0.40 | 0.40 | 0.40 |
| Maltodextrin (Maltrin M040) | 5.00 | 5.00 | 5.00 | 5.00 | 5.00 | 5.00 | 5.00 | 5.00 | 5.00 |
| Sorbitol 70% (Hexane-1,2,3,4,5,6-Hexaol) | 14.29 | 14.29 | 14.29 | 14.29 | 14.29 | 14.29 | 14.29 | 14.29 | 14.29 |
| Allantoin (2,5-Dioxo-4-Imidazolidinyl) Urea | 0.10 | 0.10 | 0.10 | 0.10 | 0.10 | 0.10 | 0.10 | 0.10 | 0.10 |
| Polyoxyethylene-polyoxypropylene Glycol | 0.20 | 0.20 | 0.20 | 0.20 | 0.20 | 0.20 | 0.20 | 0.20 | 0.20 |
| Lactic Acid 88% USP (L(+)-2-Hydroxypropanoic acid) | 4.00 | 4.00 | 4.00 | 4.00 | 4.00 | 4.00 | 4.00 | 4.00 | 4.00 |
| Bioterge PAS -8S 38% (Sodium Octane Sulfonate | 5.30 | 5.30 | 5.30 | 5.30 | 5.30 | 5.30 | 5.30 | 5.00 | 7.90 |
| Sodium Lauryl Sulfate 30% (Carsonal) | 3.33 | 2.00 | 1.33 | 0.67 | 2.66 | 1.67 | 1.67 | 0.00 | 0.00 |
| Sodium Hydroxide (50%) | 1.60 | 1.60 | 1.60 | 1.60 | 1.60 | 1.60 | 1.60 | 1.10 | 1.10 |
| FD&C Yellow # 5 | 0.03 | 0.03 | 0.03 | 0.03 | 0.03 | 0.03 | 0.03 | 0.03 | 0.03 |
| FD&C Blue # 1 | 0.02 | 0.02 | 0.02 | 0.02 | 0.02 | 0.02 | 0.02 | 0.02 | 0.02 |
| pH | 3.52 | 3.52 | 3.52 | 3.52 | 3.52 | 3.52 | 3.55 | 3.50 | 3.50 |
| Micro Test: EN 1656, 30 Seconds contact.@25° C.: Results are in Log Reduction from Initial Bacteria Count $10^8$ cfu/mL | | | | | | | | | |
| *Staphyloccocus aureus* | 7.0 | 7.0 | 7.0 | 7.0 | 7.0 | 7.0 | 5.5 | 6.5 | 5.6 |
| *Echerichia coli* | 7.0 | 7.0 | 7.0 | 7.0 | 7.0 | 7.0 | 7.0 | 5.1 | 7.0 |

TABLE II-continued

BARRIER TEAT DIP FORMULATIONS WITH LACTIC ACID, SODIUM LAURYL SULFATE AND SODIUM OCTANE SULFONATE

| Ingredients and Concentration (% w/w): Formulations Sequence | F | G | H | I | J | K | L | O | P |
|---|---|---|---|---|---|---|---|---|---|
| Blood Cell Skin Irritation Test Results: | | | | | | | | | |
| Product Haemolysis Value (H50) (ppm) | 3500 | 6300 | 9200 | | 3800 | | | 13000 | 16400 |
| Product Denaturation Index Value (DI) (%) | 9.85 | 17 | 11.87 | | | | | 0.00 | 16.2 |
| Lysis/Denaturation Ratio (L/D) (higher better) | 355.39 | 370.17 | 774.84 | | | | | NA | 1014 |

The compositions provided in Table II include both sodium octane sulfonate (SOS) and sodium lauryl sulfate (SLS) with lactic acid. As shown above, SLS is commercially available product in 30% concentration. Thus, since the values in Table II are expressed in total weight percentages, one must multiply by 0.3 to get the actual SLS content in each of the samples. Doing so, the actual SLS concentrations in composition F would be 1.0%; G would be 0.6%; H would be about 0.4%; I would be 0.2%; J would be 0.8%; and K and L would be 0.5%. The levels of SOS in each case, considering product concentration, are about 2.0% (0.38 times 5.3%).

Like with the SOS embodiments shown in Table I, the embodiments of SOS blended with SLS that are shown in Table II, are also surprisingly effective from an antimicrobial standpoint. As can be seen from Table II, the germicidal efficacy of each of the compositions F-L resulted in excess of five log reductions for both $S.\ aureus$ and $E.\ coli$. In most cases, the reductions were as high as seven log which is considered total or complete kill.

Use of SLS in combination with SOS and lactic acid produced synergistic results for kill efficacy much like those observed for combinations of SOS and lactic acid. Unfortunately, SLS is slightly more irritating to the skin than is SOS. However, because SLS is used in all of the trials at low levels (1.0% or less), the observed irritation has been found to be minimal.

Further, all of the compositions F-L possessed relatively high pH values (e.g., above 3.0) without compromising antimicrobial activity.

In Table III below, further embodiments are disclosed showing the use of a composition including Lactic Acid and SOS in as it might be used in barrier teat-dip applications.

TABLE III

BARRIER TEAT DIP FORMULATIONS WITH LACTIC ACID AND SODIUM OCTANE SULFONATE

| Ingredients and Concentration (% w/w): Formulations Sequence | Q | R | S | T | U |
|---|---|---|---|---|---|
| Water | 64.41 | 64.21 | 68.41 | 68.41 | 66.71 |
| Keltrol RD (Xantan Gum) | 0.40 | 0.40 | 0.40 | 0.40 | 040 |
| Maltodextrin (Maltrin M040) | 5.00 | 5.00 | 5.00 | 5.00 | 5.00 |
| Sorbitol 70% (Hexane-1,2,3,4,5,6-Hexaol) | 14.29 | 14.29 | 14.29 | 14.29 | 14.29 |
| Allantoin (2,5-Dioxo-4-Imidazolidinyl) Urea | 0.10 | 0.10 | 0.10 | 0.10 | 0.10 |
| Polyoxyethylene-polyoxypropylene Glycol | 0.20 | 0.20 | 0.65 | 0.65 | 0.65 |
| Lactic Acid 88% USP (L(+)-2-Hydroxypropanoic acid) | 4.00 | 4.00 | 4.00 | 4.00 | 4.00 |
| Bioterge PAS-8S 38% (Sodium Octane Sulfonate) | 5.00 | 7.20 | 0.00 | 0.00 | 6.70 |
| Sodium Lauryl Sulfate 30% (Carsonal) | 5.00 | | 5.00 | 5.00 | 0.00 |
| Benzyl Alcohol | | | 1.00 | 1.00 | 0.00 |
| Sodium Hydroxide (50%) | 1.10 | 1.30 | 1.10 | 1.10 | 1.10 |
| FD&C Yellow # 5 | 0.03 | 0.03 | 0.03 | 0.03 | 0.03 |
| FD&C Blue # 1 | 0.02 | 0.02 | 0.02 | 0.02 | 0.02 |
| pH | 3.50 | 3.54 | 3.50 | 4.00 | 3.50 |
| Micro Test: EN 1656, 30 Seconds contact.@25° C.: | | | | | |
| Results are in Log Reduction from Initial Bacteria Count $10^8$ cfu/mL | | | | | |
| Staphylaccocus aureus | 6.5 | 6.5 | 6.5 | 6.5 | 5.10 |
| Echerichia coli | 7.1 | 5.6 | 7.1 | 7.1 | 7.10 |
| Blood Cell Skin Irritation Test Results: | | | | | |
| Product Haemolysis Value (H50) (ppm) | 1850 | 3350 | 1950 | 2000 | |
| Product Denaturation Index Value (DI) (%) | 116.5 | 1.1 | 1.9 | 1.3 | |
| Lysis/Denaturation Ratio (L/D) (higher better) | 16 | 3045 | 1013 | 1538 | |

Table IV below, shows control experiments conducted using a Lactic Acid composition without the use of an anionic surfactant. As can be seen, without the synergy provided by the Lactic Acid/anionic surfactant combination, there were either minimal or no kills.

TABLE IV

BARRIER TEAT DIP FORMULATIONS: CONTROL EXPERIMENTS WITH LACTIC ACID

| Ingredients and Concentration (% w/w): Formulations Sequence | V | W | X | Y | Z |
|---|---|---|---|---|---|
| Water | | 94.40 | 92.15 | 89.15 | 86.15 | 67.51 |
| Keltrol RD (Xantan Gum) | 0.40 | 0.40 | 0.40 | 0.40 | 0.40 |

TABLE IV-continued

BARRIER TEAT DIP FORMULATIONS: CONTROL EXPERIMENTS WITH LACTIC ACID

| Ingredients and Concentration (% w/w): Formulations Sequence | V | W | X | Y | Z |
|---|---|---|---|---|---|
| Maltodextrin (Maltrin M040) | | | | | 5.00 |
| Polyvinylpyrrolidone K-30 | 0.80 | 0.80 | 0.80 | 0.80 | |
| Sorbitol 70% (Hexane-1,2,3,4,5,6-Hexaol) | | | | | 14.29 |
| Allantoin (2,5-Dioxo-4-Imidazolidinyl) Urea | | | | | 0.10 |
| Polyoxyethylene-polyoxypropylene Glycol | 0.20 | 0.20 | 0.20 | 0.20 | 0.20 |
| Polysorbate 80 (Tween 80) | 0.50 | 0.50 | 0.50 | 0.50 | 0.30 |
| PEG-7-Glyceryl Cocoate (Cetiol HE) | 0.50 | 0.50 | 0.50 | 0.50 | |
| Sodium Dioctylsulfosuccinate, 75% | 0.15 | 0.15 | 0.15 | 0.15 | 0.15 |
| EO/PO/EO Block Copolymer, Pluronic P105 | 0.50 | 0.50 | 0.50 | 0.50 | |
| Lactic Acid 88% USP (L(+)-2-Hydroxypropanoic acid) | 2.00 | 4.00 | 6.00 | 8.00 | 10.00 |
| Bioterge PAS-8S 38% (Sodium Octane Sulfonate) | | | | | |
| Sodium Lauryl Sulfate 30% (Carsonal) | | | | | |
| Sodium Hydroxide (50%) | 0.75 | 1.00 | 2.00 | 3.00 | 2.00 |
| FD&C Yellow # 5 | 0.03 | 0.03 | 0.03 | 0.03 | 0.03 |
| FD&C Blue # 1 | 0.02 | 0.02 | 0.02 | 0.02 | 0.02 |
| pH | 3.56 | 3.52 | 3.50 | 3.52 | 3.50 |
| Micro Test: EN 1656, 30 Seconds contact.@25° C.: | | | | | |
| Results are in Log Reduction from Initial Bacteria Count $10^8$ cfu/mL | | | | | |
| *Staphyloccocus aureus* | No Kill | No Kill | No Kill | No Kill | 2.8 |
| *Echerichia coli* | No Kill | No Kill | 0.9 | 1.64 | 5.1 |

Table V below shows control experiments where the use of lactic acid alone or the use of an anionic surfactant alone shows reduced kill efficacy versus a composition containing lactic acid in combination with an anionic surfactant. It should be noted that control experiments AA-AC were carried out in the presence of 10% manure or no manure, but similar results are expected when milk is present as the interferent.

TABLE V

CONTROL EXPERIMENTS WITH LACTIC ACID, SODIUM OCTANE SULFONATE AND SODIUM LAURYL SULFATE

| | AA | AB | AC |
|---|---|---|---|
| Lactic acid (adjusted to 100%) | 4.0 | 0 | 0 |
| Sodium Lauryl Sulfate (adjusted to 100%) | 0.0 | 0 | 2 |
| Sodium Octane Sulfonate (adjusted to 100%) | 0.0 | 2.2 | 0 |
| TOTAL (adjusted with water) | 100 | 100 | 100 |
| Log Kill *S. aureus*, max kill value 5, 30 sec | 0 (10% manure) | 4 (10% manure) | 0 (0% manure) |
| Log Kill *E. coli*, max kill value 5, 30 sec | 0 (10% manure) | 1 (10% manure) | 0 (0% manure) |

In Table VI below, further embodiments are disclosed showing the use of a composition including Lactic Acid and SOS in as it might be used in no-barrier teat-dip applications.

TABLE VI

NON-BARRIER TEAT DIP FORMULATIONS WITH LACTIC ACID AND SODIUM OCTANE SULFONATE

| Ingredients and Concentration (% w/w): Formulations Sequence | A | B | C | D | E | F | G | H | I |
|---|---|---|---|---|---|---|---|---|---|
| Water | 75.56 | 76.05 | 74.26 | 70.49 | 75.55 | 68.23 | 68.33 | 75.55 | 75.45 |
| Keltrol RD (Xantan Gum) | 0.40 | 0.40 | 0.40 | 0.40 | 0.40 | 0.40 | 0.40 | 0.40 | 0.40 |
| Sorbitol 70% (Hexane-1,2,3,4,5,6-Hexaol) | 14.29 | 0.00 | 14.29 | 14.29 | 0.00 | 14.29 | 14.29 | 0.00 | 0.00 |
| Glycerin | 0.00 | 10.00 | 0.00 | 0.00 | 10.00 | 0.00 | 0.00 | 10.00 | 10.00 |
| Sodium Dioctylsulfosuccinate | 0.20 | 0.20 | 0.20 | 0.20 | 0.20 | 0.20 | 0.20 | 0.20 | 0.20 |
| Polyoxyethylene-polyoxypropylene Glycol | 0.20 | 0.20 | 0.20 | 0.20 | 0.20 | 0.20 | 0.20 | 0.20 | 0.20 |
| Lactic Acid 88% USP (L(+)2-Hydroxypropanoic acid) | 4.00 | 4.00 | 4.00 | 4.00 | 4.00 | 4.00 | 4.00 | 4.00 | 4.00 |
| Bioterge PAS -8S 38% (Sodium Octane Sulfonate) | 5.30 | 7.90 | 5.30 | 7.90 | 7.90 | 10.83 | 10.83 | 7.90 | 7.90 |
| Sodium Hydroxide (50%) | 0.00 | 1.20 | 1.30 | 1.37 | 1.60 | 1.80 | 1.70 | 1.70 | 1.80 |
| FD&C Yellow # 5 | 0.03 | 0.03 | 0.03 | 0.03 | 0.03 | 0.03 | 0.03 | 0.03 | 0.03 |
| FD&C Blue # 1 | 0.02 | 0.02 | 0.02 | 0.02 | 0.02 | 0.02 | 0.02 | 0.02 | 0.02 |
| pH | 2.15 | 3.02 | 3.54 | 3.48 | 3.52 | 4.00 | 3.75 | 3.75 | 4.00 |

In Table VII below, embodiments are disclosed showing the use of a composition including Lactic Acid, SLS, and SOS in as it the composition might be used in non-barrier teat-dip applications.

TABLE VII

NON-BARRIER TEAT DIP FORMULATIONS WITH LACTIC ACID, SODIUM LAURYL SULFATE AND SODIUM OCTANE SULFONATE

| Ingredients and Concentration (% w/w): Formulations Sequence | F | G | H | I | J | K | L |
|---|---|---|---|---|---|---|---|
| Water | 70.73 | 72.06 | 72.73 | 73.39 | 70.40 | 72.39 | 86.68 |
| Keltrol RD (Xantan Gum) | 0.40 | 0.40 | 0.40 | 0.40 | 0.40 | 0.40 | 0.40 |
| Sorbitol 70% (Hexane-1,2,3,4,5,6-Hexaol) | 14.29 | 14.29 | 14.29 | 14.29 | 14.29 | 14.29 | 14.29 |
| Sodium Dioctylsulfosuccinate | 0.20 | 0.20 | 0.20 | 0.20 | 0.20 | 0.20 | 0.20 |
| Polyoxyethylene-polyoxypropylene Glycol | 0.20 | 0.20 | 0.20 | 0.20 | 0.20 | 0.20 | 0.20 |
| Lactic Acid 88% USP (L(+)-2-Hydroxypropanoic acid) | 4.00 | 4.00 | 4.00 | 4.00 | 4.00 | 4.00 | 4.00 |
| Bioterge PAS -8S 38% (Sodium Octane Sulfonate | 5.30 | 5.30 | 5.30 | 5.30 | 5.30 | 5.30 | 5.30 |
| Sodium Lauryl Sulfate 30% (Carsonal) | 3.33 | 2.00 | 1.33 | 0.67 | 2.66 | 1.67 | 1.67 |
| Sodium Hydroxide (50%) | 1.60 | 1.60 | 1.60 | 1.60 | 1.60 | 1.60 | 1.75 |
| FD&C Yellow # 5 | 0.03 | 0.03 | 0.03 | 0.03 | 0.03 | 0.03 | 0.03 |
| FD&C Blue # 1 | 0.02 | 0.02 | 0.02 | 0.02 | 0.02 | 0.02 | 0.02 |
| pH | 3.52 | 3.52 | 3.52 | 3.52 | 3.52 | 3.52 | 4.00 |

Consideration of the above, along with other test data not disclosed herein, reveals that, when presented in a ready-to-use (RTU) product for topical applications, the product components are likely to fall within the ranges set forth in Table VIII below:

TABLE VIII

READY TO USE (RTU) FORMULATIONS: RANGES OF INGREDIENTS (% W/W)

| | Preferred Range | | |
|---|---|---|---|
| Ingredient: | Broadly Preferred | Preferred | More Preferred |
| Anionic Surfactant(s) | 0.01-15 | 0.01-11.0 | 0.70-4.0 |
| Sodium Octane Sulfonate (SOS) | 0.00-10 | 0.01-8.0 | 0.70-3.0 |
| Sodium Lauryl Sulfate (SLS) | 0.00-5 | 0.00-3.0 | 0.00-1.0 |
| Lactic Acid | 0.01-20 | 2.0-6.0 | 3.0-5.0 |
| Additives | 0.00-99.9 | 5.0-30.0 | 15.0-25.0 |
| Carrier (e.g., water) | 0.01-99.9 | 1.0-90.0 | 1.5-80.0 |

Considering the above formulation embodiments along with other test data not disclosed herein, reveals that, when presented in a ready-to-use (RTU) product, where the user would mix the product with some sort of carrier (e.g., water), the product components are likely to fall within the ranges set forth in Table IX below:

TABLE IX

CONCENTRATED FORMULATIONS: RANGES OF INGREDIENTS (% W/W)

| | Preferred Range | | |
|---|---|---|---|
| Ingredient: | Broadly Preferred | Preferred | More Preferred |
| Anionic Surfactant(s) | 0.01-99.9 | 0.01-30.0 | 0.70-20.0 |
| Sodium Octane Sulfonate (SOS) | 0.00-99.9 | 0.01-20.0 | 0.70-15.0 |
| Sodium Lauryl Sulfate (SLS) | 0.00-99.9 | 0.00-10.0 | 0.00-5.0 |
| Lactic Acid | 0.01-99.9 | 4.0-30.0 | 6.0-20.0 |
| Additives | 0.00-99.9 | 8.0-50.0 | 20.0-50.0 |
| Carrier (e.g., water) | 0.01-99.9 | 1.0-70.0 | 2.0-60.0 |

It should be noted in evaluating Tables VIII and IX above that the narrowing of the ranges has been towards a composition adapted for topical applications. In other applications, e.g., surface cleaning, preferably the broad ranges would apply, and the more narrow ranges may not. For example, for some antimicrobial applications no additives would be needed, and the carrier percentages may be much lower than reflected in the "Preferred" and "More Preferred" ranges provided above. Thus, the range charts have been provided as only a depiction of embodiments of the invention, are not intended for any limiting purposes, and thus, should not be interpreted in such a manner.

Those skilled in the art will appreciate that the foregoing discussion teaches by way of example, and not by limitation. Insubstantial changes may be imposed upon the specific embodiments that are shown and described without departing from the scope and spirit of the invention.

We claim:

1. A method for controlling bovine mastitis in a bovine in need thereof comprising contacting the teats of a bovine with a nonirritating teat dip composition that consists essentially of
    about 0.02 to 30% w/w lactic acid;
    about 0.02 to 30% w/w Sodium Octane Sulfonate; an anionic surfactant; and
    an alkaline pH adjusting agent,
        wherein said composition has a half haemolysis (H50) value of at least 500 ppm, a Lysis/Denaturation (L/D) ratio greater than 100, and a pH ranging from 1.0 to about 5.0.

2. The method of claim 1, wherein the anionic surfactant is selected from the group consisting of:
    alkyl sulfonates, secondary alkane sulfonates, alkyl sulfates, alkyl ether sulfates, aryl sulfonates, aryl sulfates, alkylaryl sulfonates, alkylaryl sulfates, alkyl ether sulfonates and alkaline earth and ammonium salts and combinations thereof.

3. The method of claim 1, wherein the anionic surfactant is selected from the group consisting of:
    alkali lauryl sulfates, alkali dodecylbenzenesulfonates, alkali octane sulfonates, alkali secondary alkane sulfonates and alkali lauryl ether sulfates and alkaline earth and ammonium salts thereof.

4. The method of claim 2, wherein said anionic surfactant is Sodium Secondary Alkane Sulfonate.

5. The method of claim 3, wherein said anionic surfactant is Sodium Lauryl Sulphate (SLS).

6. The method of claim 1, wherein said composition is characterized by a Lysis/Denaturation (L/D) ratio greater than 355.39.

* * * * *